(12) United States Patent
Suzuki et al.

(10) Patent No.: US 11,384,331 B2
(45) Date of Patent: Jul. 12, 2022

(54) PARTICLE CAPTURE DEVICE

(71) Applicant: Tokyo Ohka Kogyo Co., Ltd., Kanagawa (JP)

(72) Inventors: Yasuo Suzuki, Kawasaki (JP); Atsushi Murota, Kawasaki (JP); Takashi Ohsaka, Kawasaki (JP); Toshiyuki Ogata, Kawasaki (JP)

(73) Assignee: TOKYO OHKA KOGYO CO., LTD., Kanagawa (JP)

( * ) Notice: Subject to any disclaimer, the term of this patent is extended or adjusted under 35 U.S.C. 154(b) by 219 days.

(21) Appl. No.: 16/463,060

(22) PCT Filed: Dec. 5, 2017

(86) PCT No.: PCT/JP2017/043641
§ 371 (c)(1),
(2) Date: Jun. 25, 2019

(87) PCT Pub. No.: WO2018/105608
PCT Pub. Date: Jun. 14, 2018

(65) Prior Publication Data
US 2020/0362294 A1 Nov. 19, 2020

(30) Foreign Application Priority Data
Dec. 7, 2016 (JP) .............................. JP2016-237237

(51) Int. Cl.
*G01N 37/00* (2006.01)
*C12M 1/00* (2006.01)
(52) U.S. Cl.
CPC .................................. *C12M 47/04* (2013.01)
(58) Field of Classification Search
CPC .................................................... C12M 47/04
(Continued)

(56) References Cited

U.S. PATENT DOCUMENTS 4,894,343 A * 1/1990 Tanaka .................. C12M 23/20
210/498
2010/0240041 A1 9/2010 Matsunaga et al.
(Continued)

FOREIGN PATENT DOCUMENTS

CN 1696697 11/2005
CN 1781020 5/2006
(Continued)

OTHER PUBLICATIONS

Hosokawa et al., (2010), Size-Selective Microcavity Array for Rapid and Efficient Detection of Circulating Tumor Cells, Analytical Chemistry, vol. 82, No. 15, p. 6630 (Year: 2010).*
(Continued)

*Primary Examiner* — Michael L Hobbs
*Assistant Examiner* — Lenora A Abel
(74) *Attorney, Agent, or Firm* — Wenderoth, Lind & Ponack, L.L.P.

(57) ABSTRACT

A particle capture device includes first and second substrates. The first substrate has recessed portions that have a size capable of capturing one particle. Each recessed portion has connection holes that have a size capable of allowing a dispersion medium of particles to move therethrough. A flow path that has the connection holes as an inlet port and an end portion of a first side of the first substrate as an outlet port is defined between the first substrate and the second substrate. A total opening area of the connection holes is 1 mm$^2$ or more and less than 10 mm$^2$, and a cross-sectional area of the flow path at the outlet port is 0.8 times or more the total opening area; or the total opening area is 10 mm$^2$ or more and 1000 mm$^2$ or less, and the cross-sectional area is 0.1 times or more the total opening area.

9 Claims, 7 Drawing Sheets

(58) Field of Classification Search
USPC ...................................................... 435/308.1
See application file for complete search history.

(56) References Cited

U.S. PATENT DOCUMENTS

| | | |
|---|---|---|
| 2011/0294678 A1 | 12/2011 | Jin et al. |
| 2015/0167063 A1 | 6/2015 | Shirai et al. |
| 2017/0145362 A1 | 5/2017 | Ito |
| 2018/0282677 A1 | 10/2018 | Ohsaka et al. |

FOREIGN PATENT DOCUMENTS

| | | |
|---|---|---|
| EP | 0 094 193 | 11/1983 |
| JP | 2-34597 | 8/1990 |
| JP | 2662215 | 10/1997 |
| JP | 4148367 | 9/2008 |
| JP | 2012-177686 | 9/2012 |
| JP | 2012177686 A * | 9/2012 |
| WO | 2009/016842 | 2/2009 |
| WO | 2013/019491 | 2/2013 |
| WO | 2014/020657 | 2/2014 |
| WO | 2016/020988 | 2/2016 |
| WO | 2016/038670 | 3/2016 |
| WO | 2017/057234 | 4/2017 |

OTHER PUBLICATIONS

JP2012177686A—Tanaka et al. Machine English Translation (Year: 2012).*
Extended European Search Report dated Jun. 24, 2020 in European Patent Application No. 17878020.1.
International Search Report dated Mar. 6, 2018 in International Application No. PCT/JP2017/043641.
Hosokawa et al., "Size-Selective Microcavity Array for Rapid and Efficient Detection of Circulating Tumor Cells", Anal. Chem., 2010, vol. 82, No. 15, pp. 6629-6635.
Saeki et al., "Digital cell counting device integrated with a single-cell array", PLOS ONE, Feb. 2014, vol. 9, No. 2, pp. 1-8, e89011.
Office Action dated Nov. 18, 2021 in Chinese Application No. 201780075186.9.

* cited by examiner

PARTICLE CAPTURE DEVICE

CROSS-REFERENCE TO RELATED APPLICATION

Priority is claimed from Japanese Patent Application No. 2016-237237, filed Dec. 7, 2016, the content of which is incorporated herein by reference.

TECHNICAL FIELD

In one embodiment, the present invention relates to a particle capture device.

BACKGROUND ART

There is a demand to capture and comprehensively analyze particles such as cells. For example, particularly in the field of drug discovery attempts have been made to sort and recover cells at a single cell level to use the sorted cells.

As a method for comprehensively capturing cells, for example, Patent Document 1 discloses a substrate in which cells smaller than opening portions are allowed to pass through so that desired cells are held by the opening portions by using a substrate having opening portions of different sizes on an upper surface and a lower surface for the purpose of separating specific cells of different sizes; and a method thereof.

In addition, Patent Document 2 discloses, as a substrate for capturing cells and aligning them on a plane, a cell capture substrate that has a plurality of opening portions for isolating and accommodating one cell, and has, on a bottom surface of the opening portions, a plurality of through-holes of a size that does not allow cells to pass through.

In addition, a method in which a large number of single cells are analyzed at the same time by using a microchip having wells with a size that allows only one cell to be accommodated is also known. For example, Patent Document 3 discloses a microwell array that has wells with a size that allows only one cell to be accommodated; and a screening method in which cells are cultured in the microwell array, and substances produced from the cells stored in wells are detected.

CITATION LIST

Patent Document

[Patent Document 1]
Japanese Examined Patent Application, Second Publication No. H02-34597
[Patent Document 2]
Japanese Patent No. 2662215
[Patent Document 3]
Japanese Patent No. 4148367

SUMMARY OF INVENTION

Technical Problem

Meanwhile, the inventors of the present invention have found that, in a case of capturing particles by using a particle capture device that includes a plurality of recessed portions having a size capable of capturing one particle, the particles may not be captured uniformly. Herein, the phrase "particles not captured uniformly" means that a ratio of the number of recessed portions that capture particles to the total number of recessed portions contained in a unit region on the particle capture device varies from region to region. With such background, the present invention aims to provide a technique for uniformly capturing particles.

Solution to Problem

In order to achieve the aforementioned objects, in one embodiment, the present invention is a particle capture device including a first substrate, and a second substrate that is disposed parallel to and facing a first side of the first substrate, in which the first substrate has a plurality of recessed portions that are open on a second side of the first substrate and that have a size capable of capturing one particle, the recessed portions have connection holes that connect the first side to the second side and that have a size allowing a dispersion medium of the particles to move therethrough, a flow path that has the connection holes of the first substrate as an inlet port of the dispersion medium and has an end portion of the first side of the first substrate as an outlet port of the dispersion medium is formed between the first substrate and the second substrate, the total opening area of the connection holes is 1 mm$^2$ or more and less than 10 mm$^2$ and the cross-sectional area of the flow path at the outlet port is 0.8 times or more the total opening area of the connection holes, or the total opening area of the connection holes is 10 mm$^2$ or more and 1000 mm$^2$ or less, and a cross-sectional area of the flow path at the outlet port is 0.1 times or more the total opening area of the connection holes.

In one embodiment, the present invention is a particle capture device including a first substrate, and a second substrate that is disposed parallel to and facing a first side of the first substrate, in which the first substrate has a plurality of recessed portions that are open on a second side of the first substrate and that have a size capable of capturing one particle, the recessed portion has connection holes that connect the first side to the second side and that have a size allowing a dispersion medium of the particles to move therethrough, a flow path that has the connection holes of the first substrate as an inlet port of the dispersion medium and has an end portion of the first side of the first substrate as an outlet port of the dispersion medium is formed between the first substrate and the second substrate, the total opening area of the connection holes is 1 mm$^2$ or more, and a distance between the first substrate and the second substrate is 100 μm or more.

In one embodiment, the present invention is a particle capture device including a first substrate, and a second substrate that is disposed parallel to and facing a first side of the first substrate, in which the first substrate has a plurality of recessed portions that are open on a second side of the first substrate and that have a size capable of capturing one particle, the recessed portion has connection holes that connect the first side to the second side and that have a size allowing a dispersion medium of the particles to move therethrough, a flow path that has the connection holes of the first substrate as an inlet port of the dispersion medium and has an end portion of the first side of the first substrate as an outlet port of the dispersion medium is formed between the first substrate and the second substrate, and a cross-sectional area of the flow path at the outlet port is 0.8 times or more the total opening area of the connection holes.

Advantageous Effects of Invention

According to the present invention, it is possible to provide a technique for uniformly capturing particles.

DESCRIPTION OF EMBODIMENTS

Figure 1:
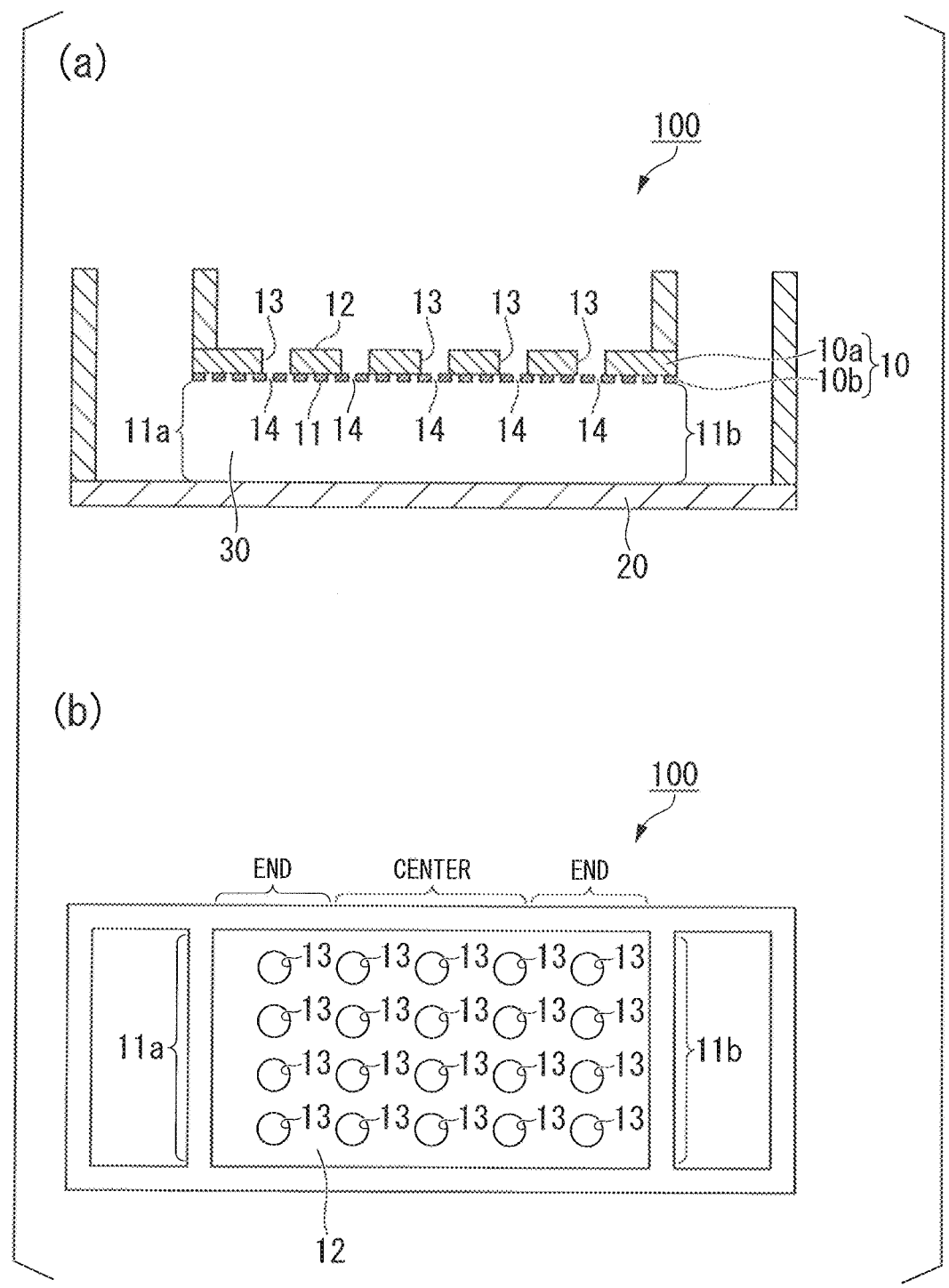
FIG. 1 is a schematic view showing an example of a particle capture device. (a) is a front cross-sectional view, and (b) is atop view.

Hereinafter, embodiments of the present invention will be described in detail with reference to the drawings in some cases. In the drawings, the same or corresponding parts are denoted by the same or corresponding reference numerals, and redundant description is not repeated. In addition, some dimensional ratios in the respective drawings are exaggerated for explanation, and thus do not necessarily correspond to actual dimensional ratios.

[Particle Capture Device]

In one embodiment, the present invention provides a particle capture device including a first substrate, and a second substrate that is disposed parallel to and facing a first side of the first substrate, in which the first substrate has a plurality of recessed portions that are open on a second side of the first substrate and that have a size capable of capturing one particle, the recessed portion has connection holes that connect the first side to the second side and that have a size allowing a dispersion medium of the particles to move therethrough, a flow path that has the connection holes of the first substrate as an inlet port of the dispersion medium and has an end portion of the first side of the first substrate as an outlet port of the dispersion medium is formed between the first substrate and the second substrate, the total opening area of the connection holes is 1 mm² or more and less than 10 mm², and a cross-sectional area of the flow path at the outlet port is 0.8 times or more the total opening area of the connection holes, or the total opening area of the connection holes is 10 mm² or more and 1000 mm² or less, and a cross-sectional area of the flow path at the outlet port is 0.1 times or more the total opening area of the connection holes. As will be described later in Examples, particles can be uniformly captured by the particle capture device of the present embodiment.

A particle capture device of the present embodiment includes a first substrate, and a second substrate that is disposed parallel to and facing a first side of the first substrate, in which the first substrate has a plurality of recessed portions that are open on a second side of the first substrate and that have a size capable of capturing one particle, the recessed portion has connection holes that connect the first side to the second side and that have a size allowing a dispersion medium of the particles to move therethrough, a flow path that has the connection holes of the first substrate as an inlet port of the dispersion medium and has an end portion of the first side of the first substrate as an outlet port of the dispersion medium is formed between the first substrate and the second substrate, the total opening area of the connection holes may be 1 mm² or more, and a distance between the first substrate and the second substrate may be 100 μm or more. As will be described later in Examples, particles can also be uniformly captured by such a particle capture device of the present embodiment.

FIGS. 1(a) and (b), FIG. 2, FIG. 3(a) to (d), FIGS. 4(a) and (b), and FIGS. 5(a) and (b) are schematic views showing an example of the particle capture device of the present embodiment. FIG. 1(a) is a front cross-sectional view, and FIG. 1(b) is a top view. In addition, FIG. 2 and FIG. 3(a) to (d) are perspective views showing an example of the particle capture device. Furthermore, FIG. 4(a) is a front cross-sectional view, and FIG. 4(b) is a top view. Furthermore, FIG. 5(a) is a front cross-sectional view, and FIG. 5(b) is a top view.

A particle capture device 100 of the present embodiment includes a first substrate 10 and a second substrate 20 that is disposed parallel to and facing a first side 11 of the first substrate 10. In addition, the first substrate 10 has a plurality of recessed portions 13 that are open on a second side 12 of the first substrate 10 and that have a size capable of capturing one particle. Furthermore, the recessed portion 13 has connection holes 14 that connect the first side 11 to the second side 12 and that have a size allowing a dispersion medium of the particles to move therethrough. Furthermore, a flow path 30 that has the connection holes 14 of the first substrate 10 as an inlet port of the dispersion medium and has end portions 11a and 11b of the first side 11 of the first substrate 10 as an outlet port of the dispersion medium is formed between the first substrate 10 and the second substrate 20. Furthermore, in a case where the total opening area of the connection holes 14 is 1 mm² or more and less than 10 mm², for example, 2 to 8 mm², the total cross-sectional area of the flow path 30 at the outlet ports 11a and 11b is 0.8 times or more the total opening area of the connection holes 14. Furthermore, in a case where the total opening area of the connection holes 14 is 10 mm² or more and 1000 mm² or less, for example, 10 to 500 mm², for example, 10 to 300 mm², for example, 10 to 100 mm², and for example, 10 to 50 mm² the total cross-sectional area of the flow path 30 at the outlet ports 11a and 11b is 0.1 times or more the total opening area of the connection holes 14.

Alternatively, in the particle capture device 100 of the present embodiment, the total opening area of the connection holes 14 may be 1 mm² or more, for example, 1 mm² to 1000 mm², for example, 1 to 500 mm², for example, 1 to 300 mm², for example, 1 to 100 mm², and for example, 1 to 50 mm²; and the distance between the first substrate and the second substrate may be 100 min or more.

In a case of the particle capture device shown in FIG. 1, an area of the outlet port is the total cross-sectional area of the flow path 30 at the end portions (11a and 11b) of the first side 11 of the first substrate 10.

As will be described later in Examples, in the particle capture device of the present embodiment, in a case where the total opening area of the connection holes 14 is 1 mm² or more and less than 10 mm², an area of the outlet port is 0.8 times or more the total opening area of the connection holes 14. Therefore, particles can be uniformly captured. In addition, in the particle capture device of the present embodiment, in a case where the total opening area of the connection holes 14 is 10 mm² or more and 1000 mm² or less, an area of the outlet port is 0.1 times or more the total opening area of the connection holes 14. Therefore, particles can be uniformly captured. Furthermore, in the particle capture device of the present embodiment, the total opening area of the connection holes 14 is 1 mm² or more, and the distance between the first substrate and the second substrate is 100 μm or more. Therefore, particles can be uniformly captured.

Figure 7:
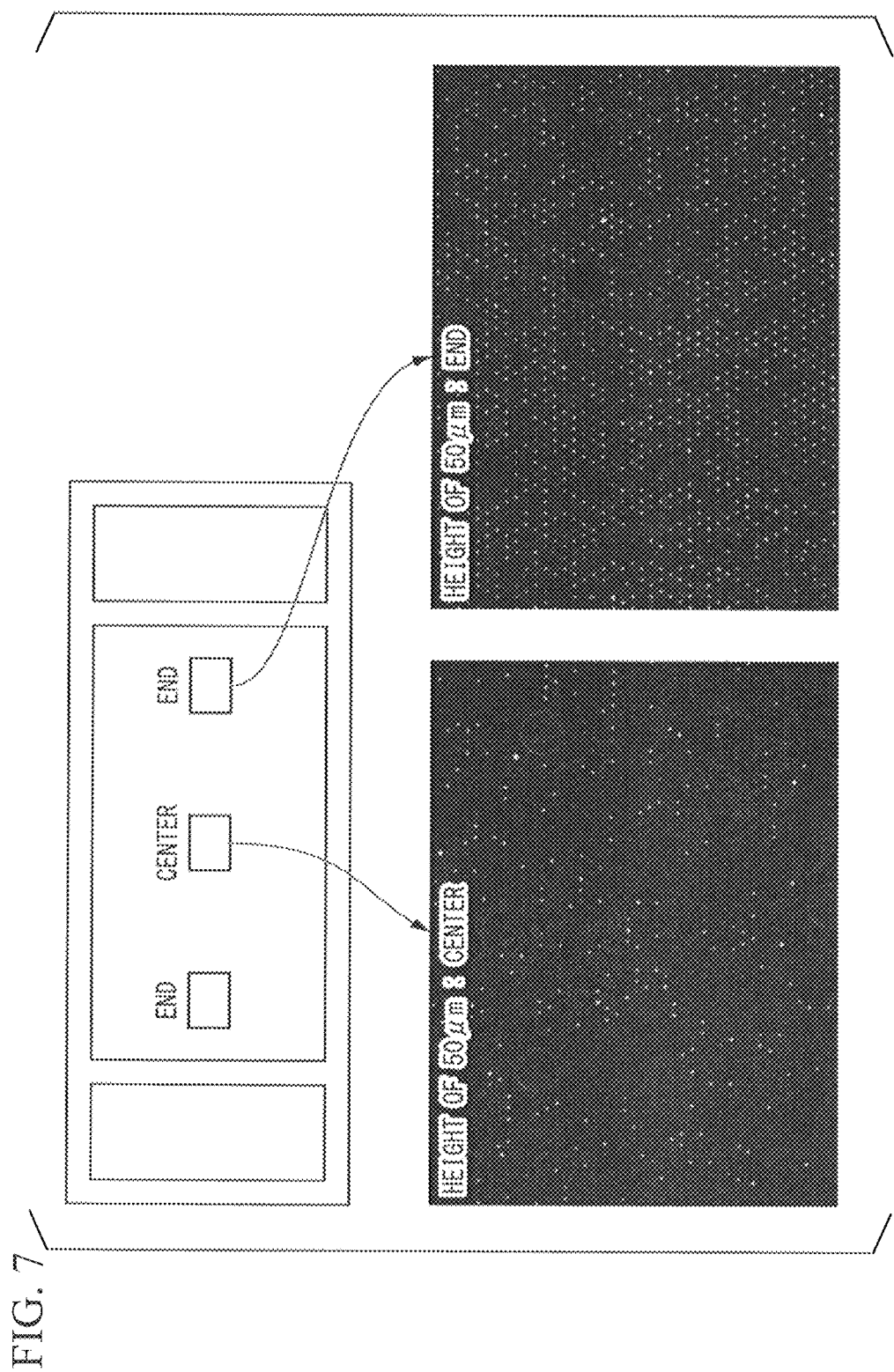
FIG. 7 shows photographs showing a result of capturing a cell with a particle capture device of Comparative Example 1 and performing fluorescence microscope observation.

As will be described later in Examples, examples of cases in which particles cannot be uniformly captured include a case in which a particle capturing ratio is low at the center portion of the particle capture device, and a particle capturing ratio is high at the end portions (portions close to the outlet ports) of the particle capture device; and the like. More specifically, photographs shown in FIG. 7 are examples thereof. In the present specification, a particle capturing ratio refers to a ratio of the total number of recessed portions contained in a unit area to the number of recessed portion that have captured particles. In addition, a unit area is not particularly limited, and may be, for example, one field of view when observed with a microscope.

Meanwhile, in the particle capture device of the present embodiment, variations between a particle capturing ratio at the center portion of the particle capture device and a particle capturing ratio at the end portion of the particle capture device are small. Therefore, according to the particle capture device of the present embodiment, particles can be uniformly captured over the whole particle capture device. In the present specification, the phrase "particle capturing ratio being uniform" is synonymous with the phrase "variations in capturing rate being small," and means that a ratio of particle capturing ratios between any regions of the particle capture device is, for example, 0.7 or more, is preferably 0.8 or more, and is more preferably 0.9 or more.

In the devices of the related art, capture of particles such as cells in the recessed portion is performed by free fall due to a weight of the particles or by a forced fall due to a centrifugal force, but a low capturing rate is a problem. On the other hand, according to the particle capture device of the present embodiment, because a flow of a liquid from the recessed portion 13 to the connection holes 14 can be generated, particles are easily captured in the recessed portion due to the flow of the liquid, and therefore a capturing rate tends to be improved.

In addition, in the devices of the related art, when attempting to recover captured particles such as cells, it is difficult to create a flow of a liquid by which particles themselves are swept away by suction from a recessed portion, and a low success rate of recovery of target particles is a problem. On the other hand, according to the particle capture device of the present embodiment, because a flow of a liquid from the flow path 30 to an opening portion of the recessed portion 13 can be generated through the connection holes 14 of the recessed portion 13, a success rate of recovery of particles tends to be improved compared to the devices of the related art.

(Particles)

In the particle capture device of the present embodiment, the particles are not particularly limited, and examples thereof include cells, cell clusters, resin particles, metal particles, glass particles, ceramic particles, and the like. The diameter of the particles is not particularly limited, and may be, for example, about 1 to 500 μm, for example, about 1 to 200 μm, for example, about 1 to 100 μm, and for example, about 1 to 50 μm. In the present specification, the diameter of particles refers to the diameter of a circle having the same area as a particle-projected area.

(Dispersion Medium)

When capturing particles, the particles that are in a state of being suspended in a dispersion medium are supplied from the second side 12 of the first substrate 10. The dispersion medium is not particularly limited, and examples thereof include water, a buffer solution, an isotonic solution, a culture medium, and the like, and these can be appropriately used according to the purpose.

(First Substrate)

As shown in FIG. 1(a), the first substrate 10 may be formed of a layer 10a in which the recessed portions 13 are patterned, and a layer 10b in which the connection holes 14 are patterned. For example, as shown in FIG. 2, the substrate 10 may have a structure in which a plurality of the recessed portions 13 are vertically and horizontally disposed at equal intervals.

Figure 2:
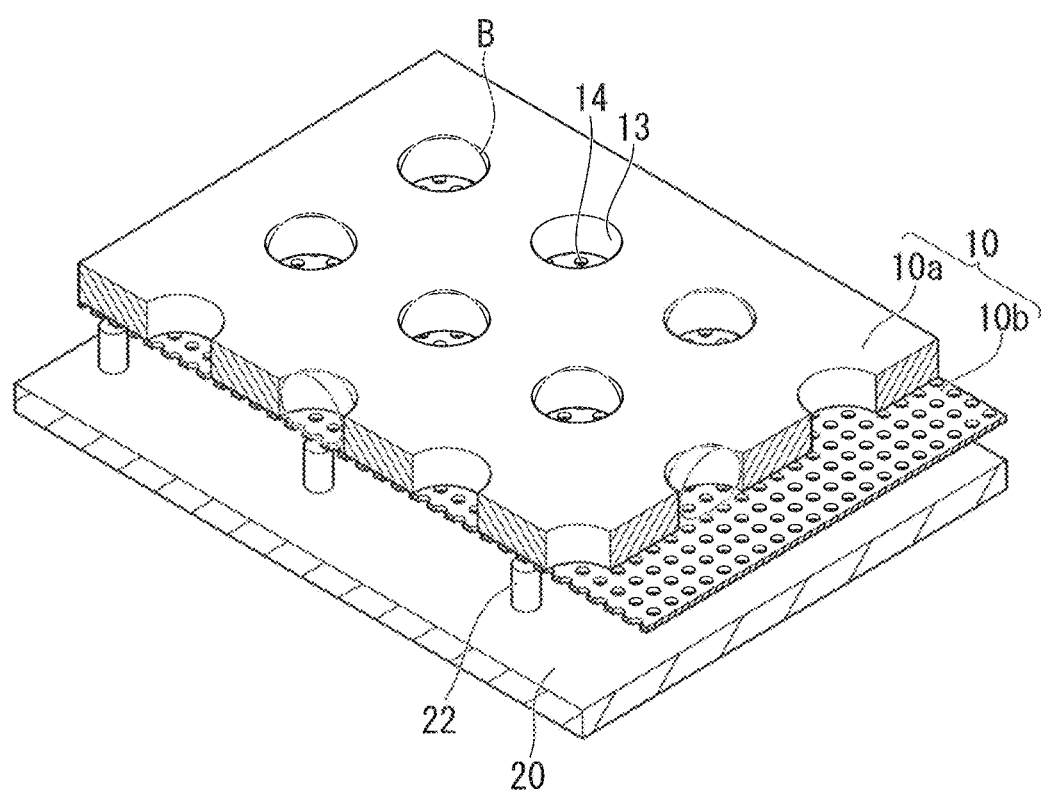
FIG. 2 is a perspective view showing an example of the particle capture device.

In FIG. 2, B represents one particle. As shown in FIG. 2, a shape of the recessed portion 13 is not particularly limited as long as one particle can be captured thereby. A shape of the recessed portion 13 may be a cylindrical shape, may be a polyhedron (for example, a rectangular parallelepiped, a hexagonal prism, an octagonal prism, and the like) constituted by a plurality of surfaces, may be an inverted truncated cone, may be an inverted truncated pyramid (inverted truncated triangle, inverted truncated square, inverted truncated pentagon, inverted truncated hexagon, or inverted truncated polygon having seven or more corners), or may be a combination shape of two or more of these shapes.

A shape of the recessed portion 13 may be, for example, a shape in which a part of the recessed portion is a cylindrical shape and the rest thereof is an inverted truncated cone shape. In a case where a shape of the recessed portion 13 is a cylindrical shape or a rectangular parallelepiped, a bottom part of the recessed portion 13 is generally flat, but may be a curved surface (a convex surface or concave surface).

The dimensions of the recessed portion 13 can be appropriately determined in consideration of a suitable ratio of the diameter of particles to be captured in the recessed portion 13 to the dimensions of the recessed portion 13. The recessed portions 13 are preferably patterned so that a form, a density, and the like thereof are controlled.

In addition, a shape and the dimensions of the recessed portion 13 are appropriately determined in consideration of the type (a shape, dimensions, and the like of a particle) of particles to be captured by the recessed portion 13 so that one particle is captured by one recessed portion 13.

In order to capture one particle with one recessed portion 13, the diameter of the largest circle that is in internal contact with a planar shape of the recessed portion 13 is preferably within a range of 0.5 to 2 times, is more preferably within a range of 0.8 to 1.9 times, and is even more preferably within a range of 0.8 to 1.8 times the diameter of particles to be captured by the recessed portion 13.

In addition, a depth of the recessed portion 13 is preferably within a range of 0.5 to 4 times, is more preferably within a range of 0.8 to 1.9 times, and even more preferably within a range of 0.8 to 1.8 times the diameter of particles to be captured by the recessed portion 13.

For example, in a case where particles to be captured are substantially spherical with a diameter of about 1 to 50 μm, the thickness of the first substrate 10, the number of the recessed portions 13, and dimensions of the recessed portion 13 are preferably as follows.

Firstly, the thickness of the first substrate 10 is preferably 1 to 100 μm, and is more preferably 10 to 50 μm. In addition, the number of the recessed portions 13 included in the first substrate 10 is not particularly limited, but is preferably within a range of, for example, 2,000 to 1,000,000 per 1 cm². Furthermore, an opening ratio of the recessed portion 13 is less than 100% in some cases due to technical problems in manufacturing. The opening ratio of the recessed portion 13 is preferably, for example, within a range of 1 to 90%.

In addition, for example, in a case where the recessed portion 13 is cylindrical, the size of the recessed portion 13 is preferably 1 to 100 μm in diameter, is more preferably 2 to 50 μm in diameter, and is even more preferably 3 to 25 μm in diameter. Furthermore, a depth of the recessed portion 13 is preferably 1 to 100 μm, is more preferably 2 to 70 μm, is even more preferably 3 to 50 μm, and is particularly preferably 4 to 30 μm. A case in which a depth of the recessed portion 13 is 1 μm or more is preferable from the viewpoint of easy capture of particles and practical use. Furthermore, a case in which the depth of the recessed part 13 is 100 μm or less is preferable from the viewpoint of a low probability of capture of a plurality of particles.

(Connection Holes)

Dimensions of the connection holes 14 can be appropriately determined in consideration of the diameter of particles to be captured by the recessed portion 13, dimensions of the recessed portion 13, characteristics of a dispersion medium for moving particles through the connection holes 14, and the like. The connection holes 14 are preferably patterned so that a form, diameter of holes, density, and the like thereof are controlled. A case in which the connection holes are controlled is preferable, because it is then easy to ensure uniformity of a permeation amount of the dispersion medium of particles. However, the connection holes 14 are not limited to holes produced by patterning, and for example, it is also possible to use holes formed by using a porous material such as a porous film.

In detail, the number, position, shape, size, and the like of the connection holes 14 are not particularly limited as long the size thereof is a size that enables capturing of particles (storing in the inside of the recessed portion 13) without allowing the particles to pass through, and moving of a dispersion medium.

Figure 3:
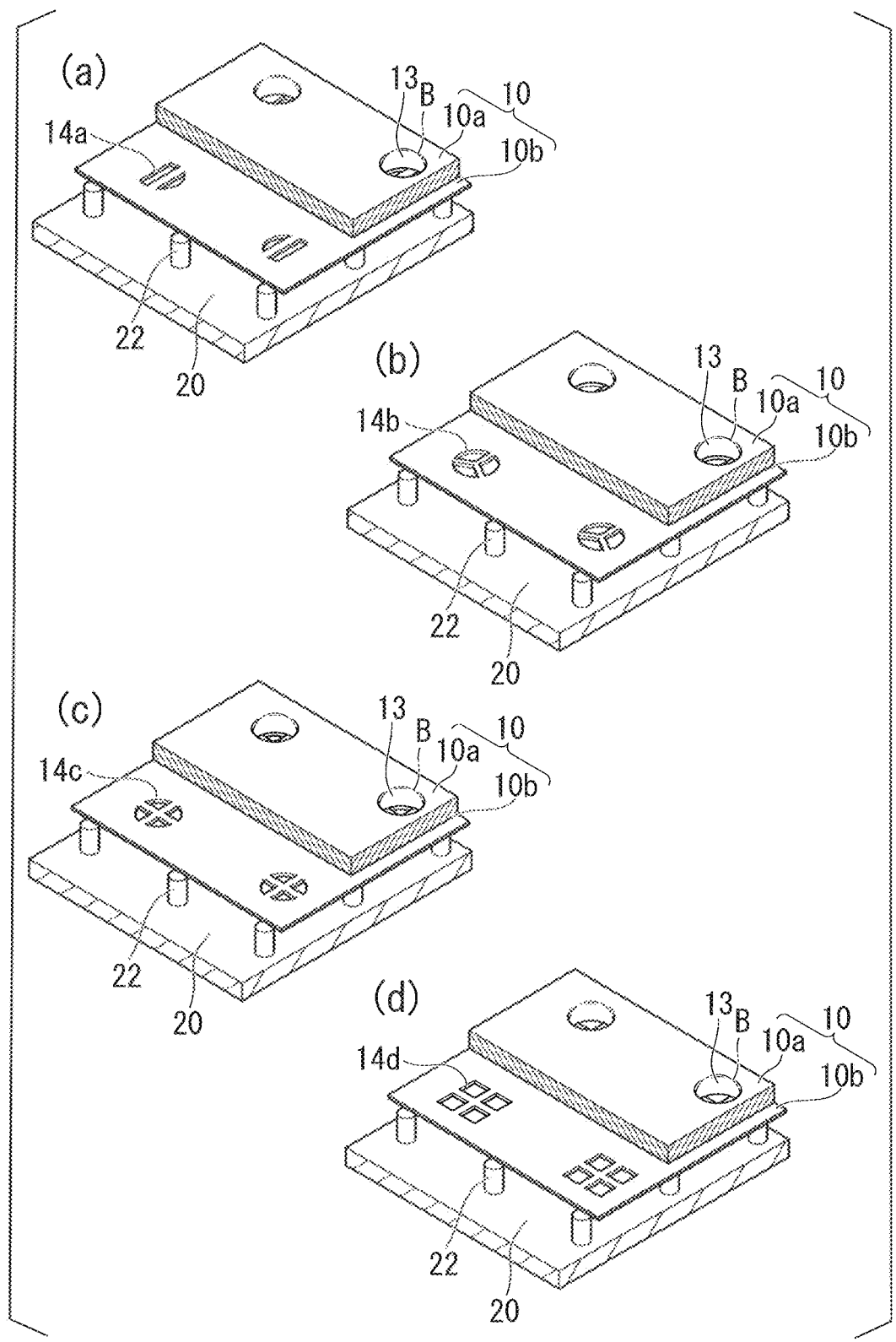
FIG. 3(a) to (d) are perspective views showing an example of the particle capture device.

For example, as shown in FIG. 2, in a case where the recessed portion 13 is cylindrical, a plurality of cylindrical connection holes 14 having a diameter smaller than the diameter of the recessed portion 13 may be provided at a bottom part of the recessed portion 13. In addition, as shown in FIG. 3, in a case where the recessed portion 13 is cylindrical, connection holes having a shape shown as 14a to 14d of FIG. 3(*a*) to (*d*) may be provided at a bottom part of the recessed portion 13.

For example, in a case where particles to be captured are substantially spherical with a diameter of about 1 to 50 μm, and the connection holes 14 are cylindrical, the diameter of the connection holes 14 is preferably 10 nm to 20 μm, is more preferably 50 nm to 15 μm, and is even more preferably 100 nm to 10 μm. In a case where the connection holes 14 has a palisading shape, a width thereof is preferably 10 nm to 20 μm, is more preferably 50 nm to 15 μm, and is even more preferably 100 nm to 10 μm. In a case where the connection holes 14 have a lattice shape, a first side is preferably 10 nm to 20 μm, is more preferably 50 nm to 15 μm, and is even more preferably 100 nm to 10 μm.

(Total Opening Area of Connection Holes)

For example, in a case where the connection holes 14 are cylindrical, cross-sectional areas of surfaces, which are parallel to the first substrate, of the connection holes 14 are constant throughout all the connection holes 14. In this case, a cross-sectional areas of a surface, which is parallel to the first substrate, at any position of the connection holes 14 may be regarded as an opening area of the connection port 14.

In addition, in a case where cross-sectional areas of surfaces, which are parallel to the first substrate, of the connection holes 14 are not constant, as an opening area of the connection port 14, the smallest cross-sectional area among cross-sectional areas of surfaces parallel to the first substrate may be regarded as an opening area of the connection port 14.

The total opening area of the connection holes 14 is an area obtained by totaling opening areas of all the connection holes 14 included in the particle capture device of the present embodiment.

(Second Substrate)

As shown in FIG. 1(*a*), the particle capture device of the present embodiment includes the second substrate 20 that is disposed parallel to and facing the first side 11 of the first substrate 10. In addition, the flow path 30 that has the connection holes 14 of the first substrate 10 as an inlet port and has the end portions 11a and 11b of the first side 11 of the first substrate 10 as an outlet port is formed between the first substrate 10 and the second substrate 20.

As shown in FIG. 2, pillars 22 that support the first substrate 10 may be present between the first substrate 10 and the second substrate 20. In a case where the pillars 22 are present, the number, position, shape, size, and the like of the pillars 22 are not particularly limited as long as the first substrate 10 can be supported and the object of the present invention can be achieved thereby.

In the particle capture device of the present embodiment, an area of the outlet port may be larger than the total opening area of the connection holes 14. As described above, in the case of the particle capture device shown in FIG. 1(*a*), the area of the outlet port is the total cross-sectional area of the flow path 30 at the end portions (11a and 11b) of the first side 11 of the first substrate 10.

In addition, in a case where the connection holes 14 are formed by using a porous material such as a porous film, an opening area of the connection holes 14 can be determined based on a void volume of the porous material. More specifically, for example, a product of the total opening area of the recessed portion 13 and a void volume of the porous, material that forms the connection holes 14 may be regarded as the total opening area of the connection holes 14.

In the particle capture device of the present embodiment, an area of the outlet port may be 1.2 times or more, may be 1.5 times or more, may be 2 times or more, may be 2.5 times or more, may be 3 times or more, may be 4 times or more, or may be 5 times or more the total opening area of the connection holes 14. The upper limit to an area of the outlet port is not particularly limited, but it is practical to set the upper limit to, for example, about 50 times the total opening area of the connection holes 14.

As will be described later in Examples, in a case where an area of the outlet port is larger than the total opening area of the connection holes 14, particles tend to be more uniformly captured.

In addition, for example, in a case where particles to be captured are substantially spherical with a diameter of about 1 to 50 μm, the distance between the first substrate 10 and the second substrate 20 may be, for example, 100 μm or more, may be, for example, 150 μm or more, may be, for example, 200 μm or more, may be, for example, 250 μm or more, may be, for example, 300 μm or more, and may be, for example, 350 μm or more. The upper limit of the distance between the first substrate 10 and the second substrate 20 is not limited from the viewpoint of a performance of the particle capture device, but is preferably 5 mm or less in consideration of practicability and the like (the amount of a dispersion medium used, the size of a microscope for observation, and the like).

As will be described later in Examples, when the distance between the first substrate 10 and the second substrate 20 is within the above-mentioned range, particles tend to be more uniformly captured.

(Material)

A material of the particle capture device of the present embodiment is not particularly limited, and is preferably a transparent material from the viewpoint of easiness of observation of particles. In addition, in a case where captured particles are observed by fluorescent observation as an index, a material is preferably a material with low autofluorescence.

As a specific material of the first substrate 10 and the second substrate 20, it is possible to use, for example, glass, and a general resin that is transparent and has low autofluorescence, such as polyethylene terephthalate (PET), polymethyl methacrylate (PMMA), polycarbonate (PC), cycloolefin polymer (COP), and epoxy.

In addition, in a case of capturing cells as particles, it is preferable that a material of the particle capture device of the present embodiment have no cell cytotoxicity and low cell adhesiveness.

The material of the particle capture device of the present embodiment is preferably polymerized by using a curable resin composition which is easy to microfabricate (hereinafter will be referred to as a "photosensitive resin composition") from the viewpoint of formation of the recessed portions 13 having a size capable of capturing one particle, and the connection holes 14 having a size allowing a dispersion medium to move therethrough.

A curable resin composition has properties of being crosslinked and cured by irradiation with active energy rays such as ultraviolet rays, and is preferably a curable resin composition which is used for a negative-type photoresist, a negative-type dry film resist, or molding of a micro resin having a fine structure. Hereinafter, a cured product obtained by curing a curable resin composition into a desired shape by photolithography will be referred to as a resin patter in some cases.

In a case where the curable resin composition is used for applications such as micro resin molding, firstly, the curable resin composition is applied to a surface of a substrate on which a resin pattern is to be formed, and a solvent component contained in the curable resin composition is volatilized to produce a resin film. Next, a photomask that becomes a shape of a pattern to be formed is placed on a surface of the resin film, and is irradiated with active energy rays such as ultraviolet rays. Thereafter, a resin pattern is formed on a surface of a substrate by subjecting it to a developing process and, if necessary, a post-baking process. This resin pattern can be used for the particle capture device of the present embodiment.

As such a curable resin composition, for example, it is possible to adopt a resin composition generally used for micro resin molding, such as a photocurable composition which contains an epoxy functional novolak resin, a cationic photopolymerization initiator such as a triarylsulfonium salt, and a diluent capable of reacting with epoxy functional groups, and which is completely cured to become a resin that is unlikely to be peeled off, a photocurable composition which contains a multifunctional bisphenol-A formaldehyde novolak resin, triphenylsulfonium hexafluoroantimonate that is an acid generator, and PGEX that is a solvent, and which becomes a resin that can form a thick film; and the like.

In addition, when a photosensitive (curable) resin composition is prepared by combining an epoxy resin and a specific acid generator, and a resin pattern is formed by using this curable resin composition, it is possible to form, with high sensitivity, a resin pattern which has a small volume shrinkage at the time of heating and curing, and has a shape in which the aspect ratio is high.

Examples of curable (photosensitive) resin compositions include a photosensitive resin composition containing a polyfunctional epoxy resin (a) and a cationic polymerization initiator (b).

<<Polyfunctional Epoxy Resin (a)>>

A polyfunctional epoxy resin used in the present embodiment may be any epoxy resin as long as it is an epoxy resin that has two or more epoxy groups in one molecule, and contains a number of epoxy groups, which is sufficient to cure a resin film formed of a curable resin composition, in one molecule. As such a polyfunctional epoxy resin, a phenol novolac-type epoxy resin, an ortho cresol novolac-type epoxy resin, a triphenyl novolac-type epoxy resin, and a bisphenol A novolac-type epoxy resin are preferable.

A functionality, which is the number of epoxy groups contained in one molecule of the polyfunctional epoxy resin, is preferably 2 or more, and is more preferably 3 to 12. A case in which the functionality of the polyfunctional epoxy resin is 3 or more is preferable because it is then possible to form a resin pattern in which an aspect ratio and resolution are high, and a case in which the functionality of the polyfunctional epoxy resin is 12 or less is preferable because it is then easy to control resin synthesis, and it is possible to suppress an excessive increase in internal stress of a resin pattern.

The mass average molecular weight of the polyfunctional epoxy resin is preferably 300 to 5,000, and is more preferably 500 to 4,000. A case in which a mass average molecular weight of the polyfunctional epoxy resin is 300 or more is preferable from the viewpoint of enabling suppression of a heat flow which may occur before a curable resin composition is cured by irradiation with active energy rays, and a case in which a mass average molecular weight of the polyfunctional epoxy resin is 5000 or less is preferable from the viewpoint of enabling obtaining of an appropriate dissolution rate at the time of patterning development.

The amount of the polyfunctional epoxy resin in the photosensitive resin composition is preferably 10 to 99.9% by mass, and is more preferably 30 to 99.9% by mass with respect to the total solid content. Accordingly, when the polyfunctional epoxy resin is coated on a substrate, a photosensitive resin film having appropriate hardness is obtained with high sensitivity.

<<Cationic Polymerization Initiator (B)>>

Next, the cationic polymerization initiator will be described. The cationic polymerization initiator is a compound in which cations are generated upon receiving irradiation with excimer laser light such as ultraviolet rays, far ultraviolet rays, KrF, and ArF, and active energy rays such as X-rays and electron beams, and these cations become a polymerization initiator.

Examples of such cationic polymerization initiators include
4-(2-chloro-4-benzoylphenylthio)phenyldiphenylsulfonium hexafluoroantimonate,
4-(2-chloro-4-benzoylphenylthio)phenyl bis(4-fluorophenyl)sulfonium hexafluoroantimonate, 4-(2-chloro-4-benzoylphenylthio)phenylbis(4-chlorophenyl)sulfonium hexafluoroantimonate,
4-(2-chloro-4-benzoylphenylthio)phenylbis(4-methylphenyl)sulfonium hexafluoroantimonate,
4-(2-chloro-4-benzoylphenylthio)phenylbis(4-β-hydroxyethoxy)phenyl)sulfonium hexafluoroantimonate,
4-(2-methyl-4-benzoylphenylthio)phenylbis(4-fluorophenyl)sulfonium hexafluoroantimonate,
4-(3-methyl-4-benzoylphenylthio)phenylbis(4-fluorophenyl)sulfonium hexafluoroantimonate,
4-(2-fluoro-4-benzoylphenylthio)phenylbis(4-fluorophenyl)sulfonium hexafluoroantimonate,
4-(2-methyl-4-benzoylphenylthio)phenylbis(4-fluorophenyl)sulfonium hexafluoroantimonate,
4-(2,3,5,6-tetramethyl-4-benzoylphenylthio)phenylbis(4-fluorophenyl)sulfonium hexafluoroantimonate,
4-(2,6-dichloro-4-benzoylphenylthio)phenylbis(4-fluorophenyl)sulfonium hexafluoroantimonate,
4-(2,6-dimethyl-4-benzoylphenylthio)phenylbis(4-fluorophenyl)sulfonium hexafluoroantimonate,
4-(2,3-dimethyl-4-benzoylphenylthio)phenylbis(4-fluorophenyl)sulfonium hexafluoroantimonate,
4-(2-methyl-4-benzoylphenylthio)phenylbis(4-chlorophenyl)sulfonium hexafluoroantimonate,
4-(3-methyl-4-benzoylphenylthio)phenylbis(4-chlorophenyl)sulfonium hexafluoroantimonate,
4-(2-fluoro-4-benzoylphenylthio)phenylbis(4-chlorophenyl)sulfonium hexafluoroantimonate,
4-(2-methyl-4-benzoylphenylthio)phenylbis(4-chlorophenyl)sulfonium hexafluoroantimonate,
4-(2,3,5,6-tetramethyl-4-benzoylphenylthio)phenylbis(4-chlorophenyl)sulfonium hexafluoroantimonate,
4-(2,6-dichloro-4-benzoylphenylthio)phenylbis(4-chlorophenyl)sulfonium hexafluoroantimonate,
4-(2,6-dimethyl-4-benzoylphenylthio)phenylbis(4-chlorophenyl)sulfonium hexafluoroantimonate,
4-(2,3-dimethyl-4-benzoylphenylthio)phenylbis(4-chlorophenyl)sulfonium hexafluoroantimonate, 4-(2-chloro-4-acetylphenylthio)phenyldiphenylsulfonium hexafluoroantimonate,
4-(2-chloro-4-(4-methylbenzoyl)phenylthio)phenyldiphenylsulfonium hexafluoroantimonate,
4-(2-chloro-4-(4-fluorobenzoyl)phenylthio)phenyldiphenylsulfonium hexafluoroantimonate,
4-(2-chloro-4-(4-methoxybenzoyl)phenylthio)phenyldiphenylsulfonium hexafluoroantimonate, 4-(2-chloro-4-dodecanoylphenylthio)phenyldiphenylsulfonium hexafluoroantimonate,
4-(2-chloro-4-acetylphenylthio)phenylbis(4-fluorophenyl)sulfonium hexafluoroantimonate,
4-(2-chloro-4-(4-methylbenzoyl)phenylthio)phenylbis(4-fluorophenyl)sulfonium hexafluoroantimonate,
4-(2-chloro-4-(4-fluorobenzoyl)phenylthio)phenylbis(4-fluorophenyl)sulfonium hexafluoroamimonate,
4-(2-chloro-4-(4-methoxybenzoyl)phenylthio)phenylbis(4-fluorophenyl)sulfonium hexafluoroantimonate,
4-(2-chloro-4-dodecanoylphenylthio)phenylbis(4-fluorophenyl)sulfonium hexafluoroantimonate,
4-(2-chloro-4-acetylphenylthio)phenylbis(4-fluorophenyl)sulfonium hexafluoroantimonate,
4-(2-chloro-4-(4-methylbenzoyl)phenylthio)phenylbis(4-chlorophenyl)sulfonium hexafluoroantimonate,
4-(2-chloro-4-(4-fluorobenzoyl)phenylthio)phenylbis(4-chlorophenyl)sulfonium hexafluoroantimonate,
4-(2-chloro-4-(4-methoxybenzoyl)phenylthio)phenylbis(4-chlorophenyl)sulfonium hexafluoroantimonate,
4-(2-chloro-4-dodecanoylphenylthio)phenylbis(4-chlorophenyl)sulfonium hexafluoroantimonate, 4-(2-chloro-4-benzoylphenylthio)phenyldiphenylsulfonium hexafluorophosphate, 4-(2-chloro-4-benzoylphenylthio)phenyldiphenylsulfonium tetrafluoroborate, 4-(2-chloro-4-benzoylphenylthio)phenyldiphenylsulfonium perchlorate,
4-(2-chloro-4-benzoylphenylthio)phenyldiphenylsulfonium trifluoromethanesulfonate,
4-(2-chloro-4-benzoylphenylthio)phenylbis(4-fluorophenyl)sulfonium hexafluorophosphate,
4-(2-chloro-4-benzoylphenylthio)phenylbis(4-fluorophenyl)sulfonium tetrafluoroborate,
4-(2-chloro-4-benzoylphenylthio)phenylbis(4-fluorophenyl)sulfonium perchlorate,
4-(2-chloro-4-benzoylphenylthio)phenylbis(4-fluorophenyl)sulfonium trifluoromethanesulfonate,
4-(2-chloro-4-benzoylphenylthio)phenylbis(4-fluorophenyl)sulfonium p-toluenesulfonate,
4-(2-chloro-4-benzoylphenylthio)phenylbis(4-fluorophenyl)sulfonium camphorsulfonate,
4-(2-chloro-4-benzoylphenylthio)phenylbis(4-fluorophenyl)sulfonium nonafluorobutanesulfonate,
4-(2-chloro-4-benzoylphenylthio)phenylbis(4-chlorophenyl)sulfonium hexafluorophosphate,
4-(2-chloro-4-benzoylphenylthio)phenylbis(4-chlorophenyl)sulfonium tetrafluoroborate,
4-(2-chloro-4-benzoylphenylthio)phenylbis(4-chlorophenyl)sulfonium perchlorate,
4-(2-chloro-4-benzoylphenylthio)phenylbis(4-chlorophenyl)sulfonium trifluoromethanesulfonate, diphenyl[4-(phenylthio)phenyl]sulfonium trifluorotrispentafluoroethyl phosphate, diphenyl[4-(p-terphenylthio)phenyl]sulfonium hexafluoroantimonate, diphenyl[4-(p-terphenylthio)phenyl]sulfonium trifluorotrispentafluoroethyl phosphate, and the like. Among these compounds, 4-(2-chloro-4-benzoylphenylthio)phenylbis(4-fluorophenyl)sulfonium hexafluoroantimonate (ADEKA Corporation, Adeka OPTOMER SP-172), diphenyl[4-(phenylthio)phenyl]sulfonium trifluorotrispentafluoroethyl phosphate (San-Apro Ltd., CPI-2105), diphenyl[4-(p-terphenylthio)phenyl]sulfonium hexafluoroantimonate, and diphenyl[4-(p-terphenylthio)phenyl]sulfonium trifluorotrispentafluoroethyl phosphate (San-Apra Ltd., HS-1PG) are preferable.

The amount of the cationic polymerization initiator in the curable resin composition is preferably 0.1 to 10% by mass, and is more preferably 0.5 to 5% by mass. A case in which the amount of the cationic polymerization initiator in the curable resin composition is 0.1% by mass or more is preferable, because then a curing time of the curable resin composition upon exposure to active energy rays can be appropriately set. In addition, a case in which the amount of the cationic polymerization initiator in the curable resin composition is 10 mass % or less is preferable, because then developability after exposure to active energy rays can be made favorable. The above-mentioned content is a content in a case where the curable resin composition does not contain a solvent component to be described later. Accordingly, in a case where the curable resin composition contains a solvent component to be described later, this is sufficient as long as the amount of the cationic polymerization initiator after removing a mass of a solvent component is within the above-mentioned range. Furthermore, it is obvious to those skilled in the art that these details of the curable resin composition can be realized based on methods known to those skilled in the art which are described in Japanese Unexamined Patent Application, First Publication No. 2008-180877 and Japanese Unexamined Patent Application, First Publication No. 2011-111588.

MODIFICATION EXAMPLES

In the particle capture device of the present embodiment, a shape of the first substrate 10, a shape of the second substrate 20, and the arrangement of the first substrate 10 and the second substrate 20 are not limited to those shown in FIG. 1(b). For example, in FIG. 1(b), although the first substrate 10 and the second substrate 20 are both rectangular, the first substrate 10 and the second substrate 20 may be, for example, circular or may be a polygon such as a triangle, pentagon, hexagon, heptagon, or octagon.

In addition, in FIG. 1(b), the first substrate 10 is disposed at the center of the second substrate 20, and outlet ports are present at two positions of 11a and 11b, but, for example, the first substrate 10 may be disposed at a position such that one end thereof is aligned with the second substrate 20, and only one of the outlet ports 11a and 11b may be present.

Modification Example 1

FIGS. 4(a) and (b) are schematic views showing an example of the particle capture device of the present embodiment. FIG. 4(a) is a front cross-sectional view, and FIG. 4(b) is a top view.

A particle capture device 400 includes a first substrate 10 and a second substrate 20 that is disposed parallel to and facing a first side 11 of the first substrate 10. In addition, the first substrate 10 has a plurality of recessed portions 13 that are open on ae second side 12 of the first substrate 10 and that have a size capable of capturing one particle. Furthermore, the recessed portion 13 has connection holes 14 that connect the first side 11 to the second side 12 and that have a size allowing a dispersion medium of the particles to move therethrough. Furthermore, a flow path 30 that has the connection holes 14 of the first substrate 10 as an inlet port of the dispersion medium and has an end portion 11a of the first side 11 of the first substrate 10 as an outlet port of the dispersion medium is formed between the first substrate 10 and the second substrate 20. Furthermore, an area of the outlet port 11a is 0.8 times or more the total opening area of the recessed portion 13. Furthermore, the relative position between the first substrate 10 and the second substrate 20 is determined by a holding member 40. In the particle capture device 400, a configuration in which the substrate 10 is held on the substrate 20 by adding pillars or the like to a lower portion of the substrate 10, instead of the holding member 40 may be adopted.

Figure 4:
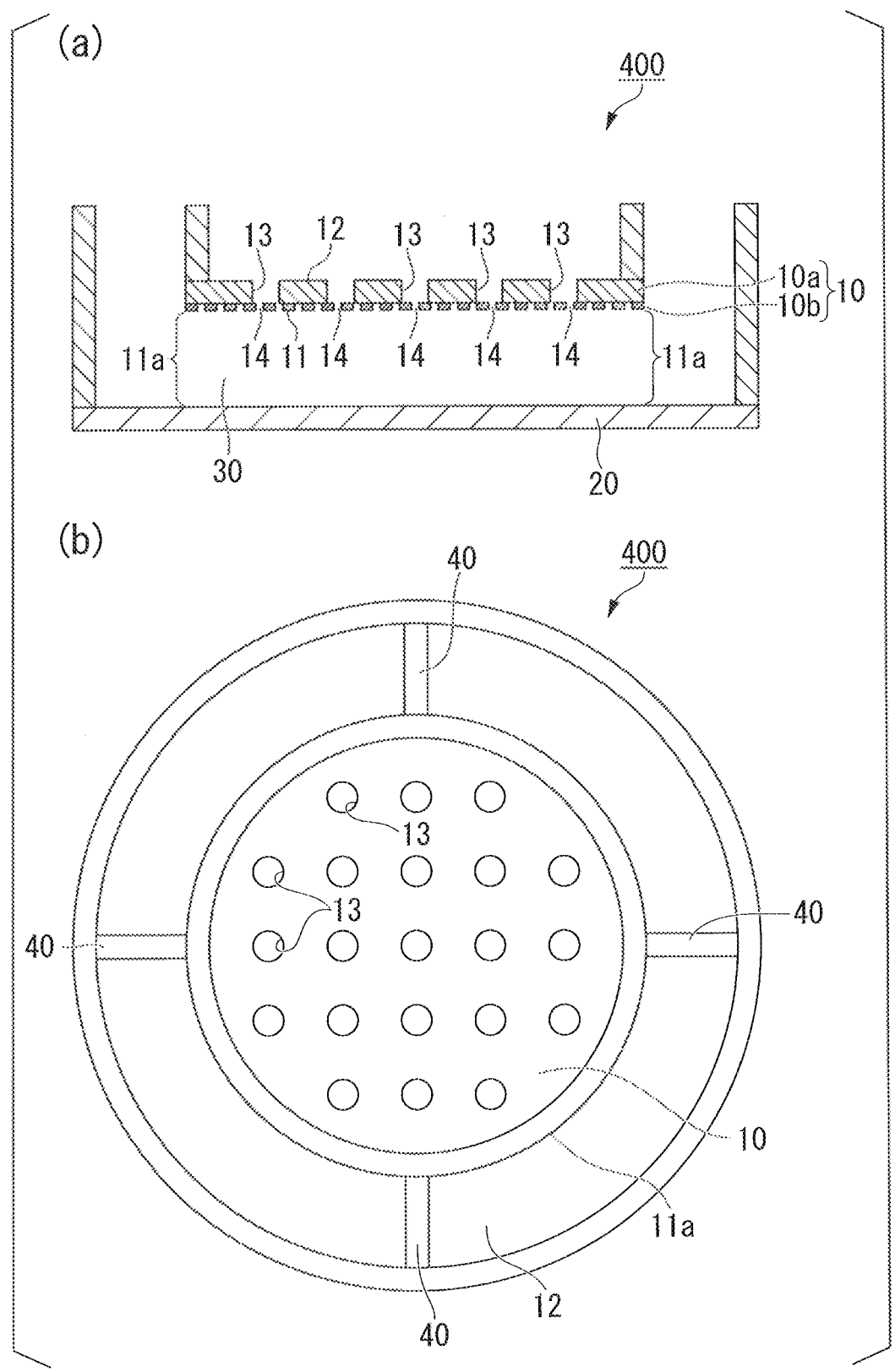
FIG. 4 is a schematic view showing an example of the particle capture device. (a) is a front cross-sectional view, and (b) is a top view.

In the particle capture device shown in FIG. 4, a planar shape of the first substrate 10 is circular. A planar shape of the second substrate 20 is also circular. For this reason, a shape of the particle capture device shown in FIG. 4 is similar to a Petri dish having two layers.

In a case of the particle capture device shown in FIG. 4, the end portion 11a of the first side 11 of the first substrate 10 is a circumference of the circular first substrate 10. Accordingly, in the particle capture device shown in FIG. 4, an area of the outlet port is a cross-sectional area of the flow path 30 circumference 11a of the first substrate 10.

Modification Example 2

FIGS. 5(a) and (b) are schematic views showing an example of the particle capture device of the present embodiment. FIG. 5(a) is a front cross-sectional view, and FIG. 5(b) is a top view.

A particle capture device 500 includes a first substrate 10 and a second substrate 20 that is disposed parallel to and facing a first side 11 of the first substrate 10. In addition, the first substrate 10 has a plurality of recessed portions 13 that are open on a second side 12 of the first substrate 10 and that have a size capable of capturing one particle. Furthermore, the recessed portion 13 has connection holes 14 that connect the first side 11 to the second side 12 and that have a size allowing a dispersion medium of the particles to prove therethrough. Furthermore, a flow path 30 that has the connection holes 14 of the first substrate 10 as an inlet port of the dispersion medium and has end portions 11a, 11b, 11c, and 11d of the first side 11 of the first substrate 10 as an outlet port of the dispersion medium is formed between the first substrate 10 and the second substrate 20. Furthermore, the total area of the outlet ports 11a, 11b, 11c, and 11d is 0.8 times or more the total opening area of the recessed portion 13. Furthermore, a relative position between the first substrate 10 and the second substrate 20 is determined by a holding member 40. In the particle capture device 500, a configuration in, which the substrate 10 is held on the substrate 20 by adding pillars or the like to a lower portion of the substrate 10, instead of the holding member 40 may be adopted.

Figure 5:
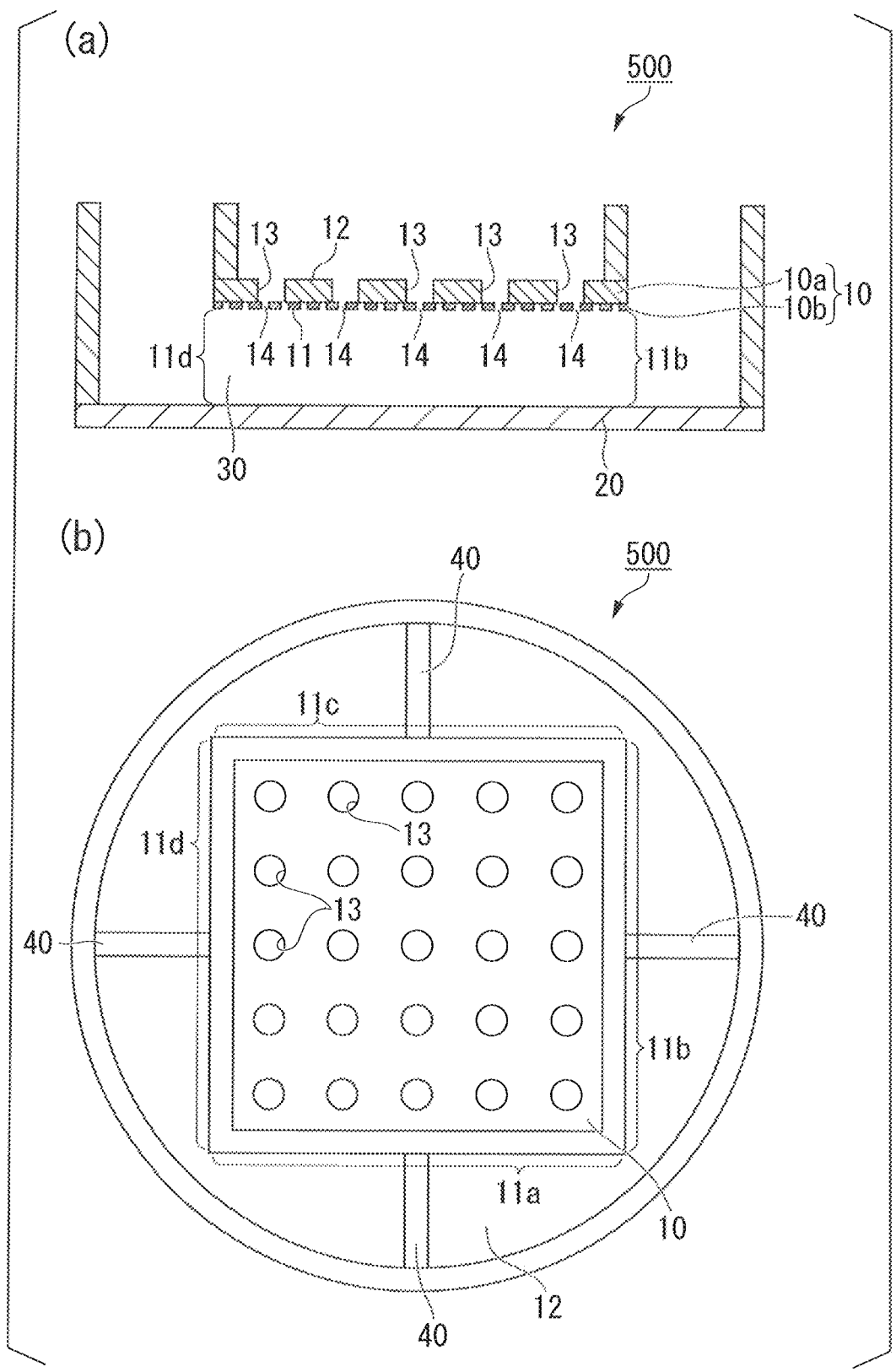
FIG. 5 is a schematic view showing an example of the particle capture device. (a) is a front cross-sectional view, and (b) is a top view.

In the particle capture device shown in FIG. 5, a planar shape of the first substrate 10 is rectangular. A planar shape of the second substrate 20 is circular.

In a case of the particle capture device shown in FIG. 5, each of the end portions 11a, 11b, 11c, and 11d of the first side 11 of the first substrate 10 forms first side of an outer circumference of the rectangular first substrate 10. Accordingly, in the particle capture device shown in FIG. 5, the area of the outlet port is the total cross-sectional area of the flow path 30 at the sides 11a, 11b, 11c, and 11d of the first substrate 10.

Modification Example 3

A plurality of the particle capture devices described above may be connected together. For example, a plurality of particle capture devices 400 or 500 described above may be connected together to form shapes such as a 6-well plate, 12-well plate, 24-well plate, 48-well plate, 96-well plate, 384-well plate, and 1536-well plate. In particular, in a case of capturing particles which are cells, the size of the particle capture device is preferably produced to be a size according to the SBS standard, a slide glass size, or a Petri dish size, which are widely used for cell culture and the like, from the viewpoint of practical use.

[Method for Manufacturing Particle Capture Device]

In one embodiment, the present invention provides a method for manufacturing the particle capture device described above. The manufacturing method of the present embodiment includes a process 1 in which a dissolvable base film is formed on a first support, a first curable resin composition is applied on the base film to form a first curable resin film, connection holes are patterned on the first curable resin film, and a support layer on which connection holes are patterned is obtained; a process 2 in which a second curable resin composition is applied on the support layer to form a second curable resin film, recessed portions are patterned on the second curable resin film, and a first substrate on which recessed portions are patterned is obtained; a process 3 in which the base film is dissolved to peel off the first substrate from the first support; and a process 4 in which the first substrate and a second substrate are bonded. The bonded product of the first substrate and the second substrate is the particle capture device.

In the manufacturing method of the present embodiment, the second substrate may have pillars. In this case, the manufacturing method of the present embodiment may include, before the process 4, a process a in which a third curable resin composition is applied on the second substrate to form a third curable resin film, pillars are patterned on the third curable resin film, and a second substrate on which the pillars are patterned is obtained.

(Process 1)

Figure 6:
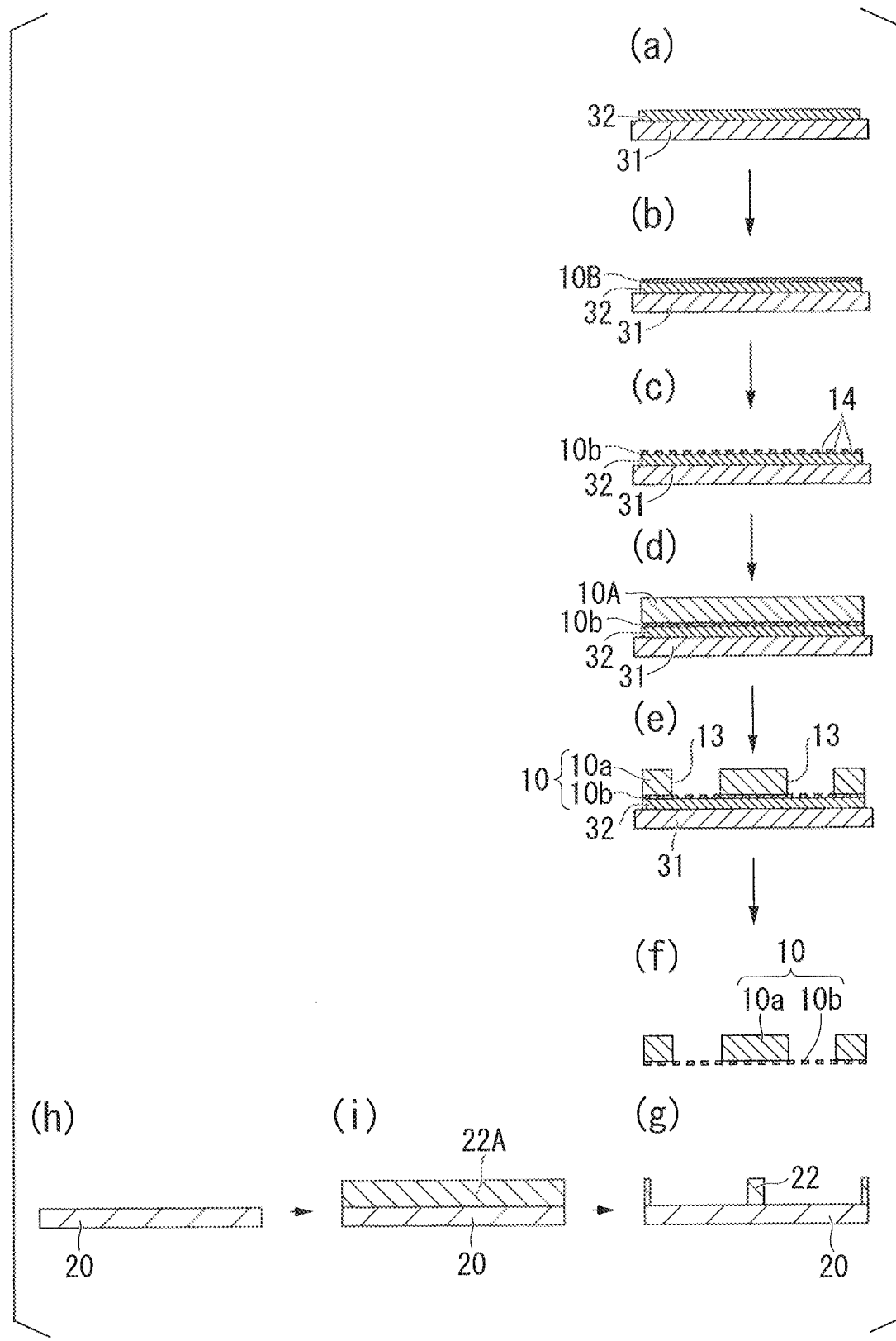
FIG. 6(a) to (i) are explanatory diagrams for a method for manufacturing a particle capture device.

In the present process, for example, as shown in FIG. 6(a), a dissolvable base film 32 is formed on a first support 31, a first curable resin composition is applied to the base film 32 to form a first curable resin film 10B, the first curable resin film 10B is exposed and then developed, and a layer 10b on which connection holes 14 are patterned as shown in as shown in FIG. 6(a) is obtained.

A method for patterning the connection holes 14 is not limited to exposure and development, and an imprint method, a method using a directed self assembly (DSA) technique, and the like may be adopted. In addition, as a method for curing the first curable resin film 10B, known methods may be adopted instead of exposure.

Examples of the first support include a substrate for electronic components, a support obtained by forming a predetermined wiring pattern on this substrate, and the like. More specific examples thereof include a silicon wafer, a metal substrate such as copper, chromium, iron, and aluminum, a glass substrate, and the like. As a material of a wiring pattern, it is possible to use, for example, copper, aluminum, nickel, gold, or the like. Examples of the first curable resin composition include the above-described curable (photosensitive) resin composition.

For the base film 32, it is possible to use polyvinyl alcohol resin, dextrin, gelatin, glue, casein, shellac, gum arabic, starch, protein, a polyacrylic acid amide, sodium polyacrylate, polyvinyl methyl ether, a styrenic elastomer, a copolymer of methyl vinyl ether and maleic acid anhydride, a copolymer of vinyl acetate and itaconic acid, polyvinyl pyrrolidone, acetyl cellulose, hydroxyethyl cellulose, sodium alginate, and the like. These materials may be a combination of a plurality of materials soluble in the same kind of liquid. From the viewpoint of hardness and flexibility of the base film, a material of the base film may contain, for example, a rubber component such as mannan, xanthan gum, or guar gum.

(Process 2)

In the present process, for example, as shown in FIG. 6(d), a second curable resin composition is applied on the layer 10b to form a second curable resin film 10A, the second curable resin film 10A is exposed and then developed, and a first substrate 10 in which the recessed portions 13 are patterned on the layer 10b is obtained.

Examples of the second curable resin composition include the above-described curable (photosensitive) resin composition. A method for patterning the recessed portions 13 is not limited to exposure and development, and an imprint method, a method using a directed self assembly (DSA) technique, and the like may be adopted. In addition, as a method for curing the second curable resin composition, known methods may be adopted instead of exposure (Process 3)

In the present process, for example, the base film 32 is dissolved by immersing the whole substrate in a release agent (for example, 1-methyl-4-isopropylcyclohexane (p-menthane)), and the first substrate 10 is peeled off from the first support 31.

(Process 4)

In the present process, the first substrate 10 shown in FIG. 6(f) which is obtained in the above-described process, and the second substrate 20 shown in FIG. 6(g) are bonded. At the time of bonding, the layer 10b is joined to face the second substrate 20. When bonding, the curable resin composition may be used as an adhesive. As shown in FIG. 6(g), the second substrate 20 may have a pillar 22.

(Process a)

In the present process, as shown in FIG. 6(i), for example, a third curable resin composition is applied on a second support 20 to form a third curable resin film 22A, the third curable resin film 22A is exposed and then developed, and a pillar pattern 22 as shown in FIG. 6(g) is formed.

The formation of the pillar pattern 22 is optional, and the present process may not be present. In addition, as a method far curing the third curable resin composition, known methods may be adopted instead of exposure. For example, a substrate for electronic components can be used as the support 20, but from the viewpoint of easy observation of captured particles, a transparent substrate is preferable, and specifically, it is preferable to adopt a glass substrate. Examples of the third curable resin composition include the above-described curable (photosensitive) resin composition.

[Method for Capturing Particles]

In one embodiment, the present invention provides a method for capturing particles which includes a process of supplying particles to the inlet port of the particle capture device described above and allowing a dispersion medium to flow out of the outlet port. The capturing method of the present embodiment can be said to be a method for capturing particles uniformly, a method for producing uniformly captured particles, and the like.

In the method for capturing particles of the present embodiment, particles supplied from the inlet port of the particle capture device described above are captured by the recessed portions 13 provided in the first substrate 10. In addition, a dispersion medium of the particles moves through the connection holes 14, passes through the flow path 30, and is discharged from the outlet port.

In the method for capturing particles of the present embodiment, particles can be uniformly captured by using the particle capture device described above.

All technical documents cited in the present specification are hereby incorporated by reference in their entirety.

The terms used in the present specification are used to describe specific embodiments and should not be understood to limit the invention. Unless otherwise specified, the terms used in the present specification (including technical terms and scientific terms) are interpreted to have the same meaning as those commonly understood by those in the skilled art in the technical field to which the present invention belongs, and therefore should not be idealized or interpreted in an overly formal sense.

The term "containing" used in the present specification is intended to mean that the described items (members, processes, elements, numbers, and the like) are present, and the term does not exclude the existence of other items (members, processes, elements, numbers, and the like), except when, the context needs to be understood in clearly different ways.

In the specification and the scope of claims, unless otherwise specified explicitly and unless there is a contradiction in the contexts, it is intended that for each of nouns described in the present specification and the scope of the claims, one or more than one objects may be present.

EXAMPLES

Hereinafter, the present invention will be described in more detail using Examples, but it is not limited to the following examples.

Example 1

(Manufacture of First Substrate)
<<Patterning of Connection Holes>>

A base agent was applied on a silicon substrate with a spin coater (1500 rpm, 20 seconds), and prebaked on a hot plate at 90° C. for 1 minute and 120° C. for 3 minutes to form a base film.

A photosensitive resin composition (refer to Japanese Unexamined Patent Application, First Publication No, 2008-180877 and Japanese Unexamined Patent Application, First Publication No. 2011-111588) was applied on the base film with a spin coater (3000 rpm, 20 seconds), and prebaked on a hot plate for 3 minutes at 90° C. Thereafter, pattern exposure (GHI rays, 150 mJ) was performed using a mirror projection mask aligner (type "MPA-600FA," manufactured by Canon), and heating was performed at 90° C. for 5 minutes with a hot plate after exposure. Thereafter, development treatment was performed for 30 seconds by an immersion method using propylene glycol monomethyl ether acetate (PGMEA). Subsequently, a resin pattern as the whole substrate after development was post-baked for 1 minute at 120° C. using an oven, and therefore a cylindrical connection hole resin pattern was obtained.

<<Patterning of Recessed Portions>>

On the connection hole resin pattern obtained above, the photosensitive resin composition was applied with a spin coater (1000 rpm, 20 seconds), and prebaked on a hot plate for 5 minutes at 90° C. Thereafter, pattern exposure (GM rays, 60 mJ) was performed using a mirror projection mask aligner (type "MPA-600FA," manufactured by Canon), and heating was performed at 90° C. for 5 minutes with a hot plate after exposure. Thereafter, development treatment was performed for 2 minutes by an immersion method using PGMEA. Subsequently, a resin pattern of the whole substrate after development was post-baked for 1 minute at 120° C. using an oven, and therefore a recessed portion pattern was obtained. The recessed portion had a cylindrical shape with a diameter of 10 μm.

(Peeling Off of First Substrate)

The first substrate on which the recessed portions obtained as above were patterned was immersed in a release agent to dissolve the above-mentioned base film, thereby peeling off the first substrate in which the recessed portion pattern was formed on the connection hole resin pattern from the silicon substrate.

(Manufacture of Second Substrate)

The photosensitive resin composition was applied on a glass substrate with a spin coater (1000 rpm, 20 seconds), and prebaked on a hot plate for 5 minutes at 90° C. Thereafter, pattern exposure (soft contact, GHI ray, 500 mJ) was performed using a parallel light exposure machine (manufactured by Hakuto Co., Ltd., model number MAT-2501), and heating was performed at 90° C. for 5 minutes with a hot plate after exposure, Thereafter, development treatment was performed for 2 minutes by an immersion method using PGMEA. Subsequently, a resin pattern of the whole substrate after development was post-baked for 1 minute at 120° C. using an oven, and therefore a resin pattern was formed on the second substrate. A resin pattern defines the distance between the first substrate and the second substrate (hereinafter referred to as a "flow path height") in a case where the first substrate and the second substrate were bonded in a process to be described later. A resin pattern in which the distance between the first substrate and the second substrate was 120 μm was produced. In addition, in a case where a flow path height was high (for example, 100 μm or more), the above-described application process with a spin coater was repeatedly performed until the height became a target height.

(Bonding of First Substrate and Second Substrate)

An adhesive was applied to a top portion of the second substrate resin pattern obtained above, and prebaked at 35° C. for 1 minute. Thereafter, the first substrate obtained above was bonded to the second substrate such that a connection hole pattern was on the bottom. Exposure (soft contact, GHI ray, 60 mJ) was performed using a parallel light exposure machine (manufactured by Hakuto Co., Ltd., model number MAT-2501), and heating was performed at 35° C. for 3 minutes and 90° C. for 1 minute with a hot plate after exposure. An adhesive was cured to bond the first substrate and the second substrate. Therefore, a particle capture device of Example 1 which has a shape shown in FIG. 1(b) was obtained.

The thickness of the first substrate was 10 μm, a pitch between recessed portions was 75 μm, and the diameter of cylindrical connection holes was 2 μm. The diameter of the recessed portions was 10 μm, and the distance between the first substrate and the second substrate was 120 μm. In addition, the size of the particle capture device was a length of 75 mm and a width of 26 mm in a plan view, which was a rectangular shape, and the thickness thereof was 15 mm.

In the particle capture device of Example 1, an area of an outlet port was 4.8 mm$^2$. The area of an outlet port was the total cross-sectional area of the flow path 30 at two places of 11a and 11b shown in FIG. 1(b). In addition, the total opening area of the connection holes was 2.7 mm$^2$. Accordingly, the area of the outlet port was about 1.78 times the total opening area of the connection holes.

Examples 2 to 11 and Comparative Examples 1 and 2

Particle capture devices of Examples 2 to 8 and Comparative Examples 1 and 2 were produced in the same manner as in Example 1, except that the shape of the device, the diameter of the recessed, portions, the height of the flow path, the total opening areas of recessed portions and connection holes, and the area of the outlet port were changed as shown in Table 1.

A particle capture device of which the device shape was a rectangle had a rectangular shape in which the length was 75 mm and a width was 26 mm in a plan view, and the thickness thereof was 15 mm. In addition, a particle capture device of which a device shape was a circular shape had a circular shape in which the outer diameter was 5.3 mm, and the thickness thereof was 1.3 mm.

Experimental Example 1

Namalwa cells suspended in a culture medium were introduced into and captured in the particle capture devices of Examples 1 to 11 and Comparative Examples 1 and 2. Namalwa cells were stained with Calcein-AM (manufactured by DOJINDO LABORATORIES) in advance. The number of Namalwa cells introduced into the particle capture device was equal to the number of recessed portions of each of the particle capture devices.

Subsequently, fluorescence microscope observation (object lens magnification of 4×, model "BZ-9000," KEYENCE CORPORATION) was performed on a center portion and an end portion of the particle capture device, and the number of captured cells in one field of view was measured. The measurement results of the particle capture devices of Examples 1 to 11 and Comparative Examples 1 and 2 are shown in Table 1.

In Table 1, an "area ratio" indicates a ratio of the area of the outlet port to the total opening area of the connection holes of the particle capture device. In addition, a "cell number ratio" indicates a ratio of the number of cells in the center portion to the number of cells in the end portion of the particle capture device in one field of view when observed with a fluorescence microscope. This value is identical to the ratio of a capturing rate of cells in the center portion to a capturing rate of cells in the end portion of the particle capture device.

TABLE 1

|  | Device shape | Diameter of recessed portion (μm) | Height of flow path (μm) | Total opening area of connection hole (mm²) | Cross-sectional area of outlet port (mm²) | Area ratio | Cell number ratio |
|---|---|---|---|---|---|---|---|
| Example 1 | Rectangular shape | 10 | 120 | 2.7 | 4.8 | 1.78 | 0.87 |
| Example 2 | Rectangular shape | 10 | 200 | 2.7 | 8.0 | 2.96 | 0.91 |
| Example 3 | Rectangular shape | 10 | 340 | 2.7 | 13.6 | 5.03 | 0.86 |
| Example 4 | Rectangular shape | 15 | 120 | 6.0 | 4.8 | 0.8 | 0.78 |
| Example 5 | Rectangular shape | 15 | 200 | 6.0 | 8.0 | 1.33 | 0.79 |
| Example 6 | Rectangular shape | 15 | 340 | 6.0 | 13.6 | 2.27 | 0.86 |
| Example 7 | Circular shape | 10 | 70 | 2.4 | 8.4 | 3.4 | 0.77 |
| Example 8 | Circular shape | 10 | 140 | 2.4 | 16.7 | 6.9 | 0.79 |
| Example 9 | Rectangular shape | 15 | 120 | 19 | 4.8 | 0.26 | 0.84 |
| Example 10 | Rectangular shape | 15 | 200 | 19 | 8.0 | 0.43 | 0.85 |
| Example 11 | Rectangular shape | 15 | 340 | 19 | 13.6 | 0.73 | 0.86 |
| Comparative Example 1 | Rectangular shape | 10 | 50 | 2.7 | 2.0 | 0.74 | 0.28 |
| Comparative Example 2 | Rectangular shape | 15 | 50 | 6.0 | 2.0 | 0.33 | 0.57 |

Furthermore, FIG. 7 is a photograph which shows the results of performing fluorescence microscope observation on the center portion and the end portion of the particle capture device, after capturing Namalwa cells with the particle capture device of Comparative Example 1 as an example. As shown in FIG. 7, in the particle capture device of Comparative Example 1, a capturing rate of cells differed depending on the position of the particle capture device.

INDUSTRIAL APPLICABILITY

According to the present invention, it is possible to provide a technique for uniformly capturing particles.

REFERENCE SIGNS LIST

10 First substrate
10a, 10b Layer
10A Second curable resin film
10B First curable resin film
11 First side
12 Second side
13 Recessed portion
14, 14a, 14b, 14c, 14d Connection hole
11a, 11b End portion (outlet port)
20 Second substrate
22 Pillar
22A Third curable resin film
30 Flow path
31 First support
32 Base film
100, 400, 500 Particle capture device
B Particle

What is claimed is:

1. A particle capture device comprising:
a first substrate; and
a second substrate that is parallel to and faces a first side of the first substrate,
wherein:
the first substrate has a plurality of recessed portions that are open on a second side of the first substrate and that have a size capable of capturing one particle of a dispersion medium of a plurality of particles;
each of the plurality of recessed portions has connection holes that connect the first side of the first substrate to the second side of the first substrate and that have a size capable of allowing the dispersion medium of the plurality of particles to move therethrough;
a flow path that has the connection holes of the first substrate as an inlet port of the dispersion medium and has an end portion of the first side of the first substrate as an outlet port of the dispersion medium is defined between the first substrate and the second substrate; and
a total opening area of the connection holes is 10 mm² or more and 1000 mm² or less, and a cross-sectional area of the flow path at the outlet port is 0.1 times or more the total opening area of the connection holes.

2. The particle capture device according to claim 1, wherein the cross-sectional area of the flow path at the outlet port is larger than the total opening area of the connection holes.

3. The particle capture device according to claim 1, wherein a distance between the first substrate and the second substrate is 100 μm or more.

4. The particle capture device according to claim 1, wherein a diameter of the one particle is 1 μm to 500 μm.

5. A particle capture device comprising:
a first substrate; and
a second substrate that is parallel to and faces a first side of the first substrate,
wherein:

the first substrate has a plurality of recessed portions that are open on a second side of the first substrate and that have a size capable of capturing one particle of a dispersion medium of a plurality of particles;

each of the plurality of recessed portions has connection holes that connect the first side of the first substrate to the second side of the first substrate and that have a size capable of allowing the dispersion medium of the plurality of particles to move therethrough;

a flow path that has the connection holes of the first substrate as an inlet port of the dispersion medium and has an end portion of the first side of the first substrate as an outlet port of the dispersion medium is defined between the first substrate and the second substrate;

a total opening area of the connection holes is 10 mm$^2$ or more; and a distance between the first substrate and the second substrate is 100 μm or more.

6. The particle capture device according to claim 2, wherein a distance between the first substrate and the second substrate is 100 μm or more.

7. The particle capture device according to claim 2, wherein a diameter of the one particle is 1 μm to 500 μm.

8. The particle capture device according to claim 3, wherein a diameter of the one particle is 1 μm to 500 μm.

9. The particle capture device according to claim 6, wherein a diameter of the one particle is 1 μm to 500 μm.

* * * * *